United States Patent
McKee et al.

(10) Patent No.: US 10,598,659 B2
(45) Date of Patent: Mar. 24, 2020

(54) LATERAL FLOW BLOTTING ASSAY

(71) Applicant: Bio-Rad Laboratories, Inc., Hercules, CA (US)

(72) Inventors: Clayton T. McKee, Davis, CA (US); William Strong, El Cerrito, CA (US); Mingde Zhu, Hercules, CA (US); Emmanuel Quiroz, San Leandro, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 374 days.

(21) Appl. No.: 15/388,778

(22) Filed: Dec. 22, 2016

(65) Prior Publication Data

US 2017/0191997 A1    Jul. 6, 2017

Related U.S. Application Data

(60) Provisional application No. 62/273,055, filed on Dec. 30, 2015.

(51) Int. Cl.
*G01N 33/543* (2006.01)
*G01N 33/558* (2006.01)

(52) U.S. Cl.
CPC ..... *G01N 33/558* (2013.01); *G01N 33/54386* (2013.01)

(58) Field of Classification Search
None
See application file for complete search history.

(56) References Cited

U.S. PATENT DOCUMENTS

| 4,981,786 A * | 1/1991 | Dafforn | G01N 33/5302 422/412 |
| 5,354,692 A * | 10/1994 | Yang | G01N 33/558 422/412 |
| 2008/0199851 A1 | 8/2008 | Egan et al. | |
| 2012/0094276 A1 | 4/2012 | Buchanan | |
| 2012/0220049 A1 | 8/2012 | Bunce et al. | |
| 2015/0024415 A1 | 1/2015 | Lu et al. | |
| 2015/0241425 A1 | 8/2015 | McKee | |

FOREIGN PATENT DOCUMENTS

WO    2008/016268 A1    2/2008

OTHER PUBLICATIONS

International Search Report and Written Opinion from Application No. PCT/US2016/068414, dated Mar. 2, 2017.
Extended European Search Report in EP Application 16882447.2 dated May 9, 2019; 8 pages.

* cited by examiner

*Primary Examiner* — Rebecca L Martinez
(74) *Attorney, Agent, or Firm* — Kilpatrick Townsend and Stockton LLP (57) ABSTRACT

A lateral flow apparatus is provided.

17 Claims, 4 Drawing Sheets

LATERAL FLOW BLOTTING ASSAY

CROSS-REFERENCE TO RELATED PATENT APPLICATIONS

The present patent application claims benefit of priority to U.S. Provisional Patent Application No. 62/273,055, filed Dec. 30, 2015, which is incorporated by reference for all purposes.

BACKGROUND OF THE INVENTION

Methods for detection of immobilized analytes are commonly employed in the biological sciences. For example, traditional blotting (e.g., Southern, northern, western, far western, eastern, vacuum, middle eastern, eastern-western, and far-eastern blotting, etc.) can be used to detect analytes immobilized on a substrate or membrane or in a matrix (e.g., in agarose or acrylamide). In general, such blotting techniques involve immobilization of the analyte(s) to be detected and contacting the analyte(s) with a binding reagent (e.g., an antibody). Blotting also usually involves multiple washing steps and/or blocking steps between immobilization and final detection. Such washing and blocking steps consume a practitioner's limited time and/or reagents and can be a source of error and irreproducibility.

BRIEF SUMMARY OF THE INVENTION

Provided herein is a lateral flow apparatus. In some embodiments, the apparatus is a single use, disposable apparatus. In some embodiments, the apparatus comprises, a wicking pad composed of a porous substrate, the wicking pad having:
(i) a region for applying a membrane comprising immobilized analytes (e.g., proteins); and
(ii) a region for applying primary antibodies; and
wherein the wicking pad has:
a first edge and a second edge and two lateral edges,
a first reservoir comprising a first absorbent pad adjacent to the first side of the wicking pad; and
a second reservoir comprising a second absorbent pad adjacent to the second side of the wicking pad.

In some embodiments, the wicking pad further comprises:
(iii) a region for applying secondary antibodies or other secondary detection reagents.

In some embodiments, the apparatus is sealed in a plastic casing. In some embodiments, the plastic casing comprises a molded top portion and a flat bottom plate sealed to the top portion. In some embodiments, the molded top portion comprises a port(s) covered by a removable layer over the first reservoir and/or second reservoirs to allow application of liquid through the port to the first reservoir and to allow for passage of air to relieve pressure in the second reservoir (the second reservoir casing can alternatively optionally include holes to allow for air flow that are not covered). In some embodiments, the removable cover is composed of a metal or plastic foil. In some embodiments, the molded top portion comprises a lid over the regions (i), (ii), and (iii) to allow for access to the regions and subsequent closing of the lid. In some embodiments, the lid comprises one or more port to allow for delivery of reagents through the port to the wicking pad when the lid is closed.

In some embodiments, the region for applying primary antibodies is between the first reservoir and the region for applying a membrane comprising proteins, and wherein the molded top portion of the plastic casing has: a user-accessible port to allow for delivery of liquid to the first reservoir and lacks a user-accessible port to access the second reservoir. In some embodiments, the region for applying primary antibodies is between the first reservoir and the region for applying a membrane comprising proteins, and wherein the molded top portion of the plastic casing has: a user-accessible port to allow for delivery of liquid to the first reservoir and a user-accessible port to allow to allow for air flow to the second reservoir.

In some embodiments, at least one of the reservoirs is separated from the wicking pad by a removable non-absorbent strip.

In some embodiments, the wicking pad and reservoirs are dry.

In some embodiments, at least one of the wicking pad, and the first reservoir is wet.

In some embodiments, the region for applying secondary antibodies on the wicking pad comprises dried secondary antibodies embedded in the wicking pad. In some embodiments, the wicking pad comprises a slot configured to receive an absorbent strip comprising secondary antibodies.

In some embodiments, the region for applying primary antibodies on the wicking pad comprises dried primary antibodies embedded in the wicking pad. In some embodiments, the wicking pad comprises a slot configured to receive an absorbent strip comprising primary antibodies.

Also provided is a kit for performing lateral flow. In some embodiments, the kit comprises, the lateral flow apparatus as described above or elsewhere herein. In some embodiments, the kit further comprises a secondary antibody or secondary detection reagent. In some embodiments, the secondary antibody or detection reagent is in liquid form. In some embodiments, the secondary antibody or detection reagent is embedded on a strip. In some embodiments, the strip is dry. In some embodiments, the strip is wet.

In some embodiments, the kit further comprises a primary antibody. In some embodiments, the primary antibody is in liquid form. In some embodiments, the primary antibody is embedded on a strip. In some embodiments, the strip is dry. In some embodiments, the strip is wet. In some embodiments, the primary and/or secondary antibody are prelabeled with a reporter molecule. In other embodiments the primary and/or secondary antibody are labeled with a molecule (e.g., biotin or streptavidin, for example) that interacts or reacts with a reporter molecule.

In some embodiments, the kit further comprises a strip lacking antibodies that is suitable to user-application of antibodies or detection reagents. In some embodiments the kit contains a reagent or solution for performing lateral flow (running buffer) and optionally may contain blocking agents, surfactants, agents to prevent protein aggregation, agents to promote complete even flow of reagents and/or promote reaction to molecules on the membrane and minimize background on the membrane.

Also provided are methods of performing a lateral flow western blot assay. In some embodiments, the method comprises the lateral flow apparatus as described above or elsewhere herein; applying running buffer to the first reservoir and the wicking pad; applying a membrane comprising analytes or proteins (e.g., western blot) to the region (i) for applying a membrane comprising proteins; applying primary antibodies to the region (ii) for applying primary antibodies; and allowing lateral flow of the running buffer from the first reservoir to the second reservoir such that the primary antibodies are transported in the wicking pad and are contacted to the proteins in the membrane, wherein the primary antibodies bind to their target proteins, if present, in the membrane.

In some embodiments, the apparatus is sealed in a plastic casing, wherein the plastic casing comprises a molded top portion and a flat bottom plate sealed to the top portion and the molded top portion comprises removable a layer over the first reservoir to allow application of liquid and a lid over the regions (i) and (ii) to allow for access to the regions and subsequent closing of the lid; and the method further comprises:

removing the layer over the first reservoir and applying running buffer to the first reservoir; and opening the lid and applying running buffer and the membrane to the wicking pad and subsequently closing the lid to allow for lateral flow from the first reservoir to the second reservoir.

In some embodiments, said applying primary antibodies to the region (ii) for applying primary antibodies comprises contacting a porous strip comprising dried embedded primary antibodies to the wicking pad such that the primary antibodies are eluted form the porous trip to the wicking pad.

In some embodiments, the method further comprises applying secondary antibodies or secondary detection reagents to the wicking pad such that the secondary antibodies or secondary detection reagents flow by lateral flow through the wicking pad and into the membrane after the primary antibodies contact the membrane. In some embodiments, said applying secondary antibodies or secondary detection reagents to the wicking pad comprises contacting a porous strip comprising dried embedded secondary antibodies to the wicking pad such that the secondary antibodies or secondary detection reagents are eluted form the porous trip to the wicking pad.

In some embodiments, the method further comprises following binding of the primary antibodies to the target proteins, if present, (and optionally contact of the secondary antibodies or secondary detection regents to the primary antibodies), removing the membrane and detecting the binding of the primary antibodies to the target proteins if present. In some embodiments, the primary antibodies are applied to the wicking pad through one or more port in the lid.

I. DEFINITIONS

The term "analyte" refers to a biological molecule, e.g., a protein, nucleic acid, polysaccharide, lipid, antigen, growth factor, hapten, etc., or a portion thereof. Analytes can be irreversibly immobilized on a surface, such as a membrane and detected as described herein.

The term "immobilized" as used herein refers to reversibly or irreversibly immobilized molecules (e.g., binding reagents or analytes). Reversibly immobilized molecules are immobilized in a manner that allows the molecules, or a portion thereof (e.g., at least 25%, 50%, 60%, 75%, 80% or more of the molecules), to be removed from their immobilized location without substantial denaturation or aggregation. For example, a molecule can be reversibly immobilized in or on a porous substrate by contacting a solution containing the molecule with the porous substrate, thereby soaking up the solution and reversibly immobilizing the molecule. The reversibly immobilized molecule can then be removed by wicking the solution from the porous substrate, or from one region of the porous substrate to another. In some cases, a molecule can be reversibly immobilized on a porous substrate by contacting a solution containing the molecule with the porous substrate, thereby soaking up the solution, and then drying the solution containing porous substrate. The reversibly immobilized molecule can then be removed by contacting the porous substrate with another solution of the same or a different composition, thereby solubilizing the reversibly immobilized molecule, and then wicking the solution from the porous substrate, or from one region of the porous substrate to another.

Irreversibly immobilized molecules (e.g., binding reagents or analytes) are immobilized such that they are not removed, or not substantially removed, from their location under mild conditions (e.g., pH between about 4-9, temperature of between about 4-65° C.). Exemplary irreversibly immobilized molecules include protein analytes bound to a nitrocellulose or polyvinylidene fluoride membrane by standard blotting techniques (e.g., electroblotting).

The term "binding reagent" refers to a reagent that specifically binds to a molecule such as an analyte. While antibodies are described in many contexts herein, it will be understood that other binding agents can be used instead of antibodies as preferred by the user. A wide variety of binding reagents are known in the art, including antibodies, aptamers, affimers, lipocalins (e.g., anticalins), thioredoxin A, bilin binding protein, or proteins containing an ankyrin repeat, the Z domain of staphylococcal protein A, or a fibronectin type III domain.

The term "specifically bind" refers to a molecule (e.g., binding reagent such as an antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, 100-fold, or 1000-fold or more greater affinity.

The term "antibody" refers to a polypeptide comprising a framework region from an immunoglobulin gene, or fragments thereof, that specifically bind and recognize an antigen, e.g., a particular analyte. Typically, the "variable region" contains the antigen-binding region of the antibody (or its functional equivalent) and is most critical in specificity and affinity of binding. See Paul, *Fundamental Immunology* (2003). Antibodies include for example chimeric, human, humanized antibodies, or single-chain antibodies.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

DETAILED DESCRIPTION OF THE INVENTION

The inventors have discovered useful lateral flow apparatus configurations for allowing for efficient lateral flow detection of proteins on membranes (e.g., western blots) using specific binding reagents (e.g., antibodies). In some embodiments, the apparatus described herein can be configured in a single-use casing allowing for an affordable and simple assay format.

The lateral flow configurations described herein involve a first reservoir that acts to supply liquid (buffer), a wicking pad where reagents and one or more membrane comprising proteins or other analytes to be detected can be placed, and a second reservoir that acts as a pump by wicking the liquid to the dry second reservoir.

The first reservoir can include one or more absorbent pad encased in a water proof cover. The reservoir is in liquid communication with the wicking pad (i.e., liquid, when present in the first reservoir) can flow from the first reservoir to the wicking pad). The waterproof cover can comprise one or more port, optionally covered with a removable cover layer, such that the port can be used to deliver fluid (e.g., blocking buffer, running buffer) to the reservoir when the apparatus is going to be put into use. An exemplary blocking buffer can include, for example, casein, non-fat milk, synthetic blockers, gelatin, bovine serum albumen (BSA), detergents and/or surfactants, buffers and salts, including but not limited to Tris-buffered saline, 0.1% Tween 20 (TBST) or phosphate buffered saline with Tween 20 or Triton X-100 (PBST), for example as typically used with western blotting. The salt concentration and blockers in the buffer can be used for controlling background for optimal signal to noise in the lateral flow assay.

The wicking pad is a flat absorbent material onto which can be placed detection reagents (e.g., antibodies) and the membrane comprising immobilized analytes or proteins (e.g., a western blot). The wicking pad may include drawings/markings or other indications for where a user should place the detection reagents or membrane. Alternately, the drawing/markings may be on the lid or casing.

The wicking pad material will generally be a bibulous material and can be made out of for example, natural, synthetic, glass fibers or blends thereof. Non-limiting examples include cotton/cellulose, glass, polyacrylate, rayon, polypropylene, and combinations thereof. There are many commercial materials available for diagnostic uses from vendors such as Ahlstrom, Whatman (GE), PALL, Millipore, Sartorius, S&S etc. In some embodiments, the wick pad may be backed to prevent flow on the underside. This can be achieved for example using an adhesive backing to which the wick pad is adhered. The nature of the adhesive may affect the assay performance (i.e., flow characteristics, reagent stability etc.) so this can be optimized for the desired assay or application. In some embodiments, the adhesive may be part of the flat sealed side of the device.

While the membrane comprising immobilized analytes to be detected will be generally provided by the user, in some embodiments, the wicking pad will have embedded detection reagents. For instance, in some embodiments, primary or secondary antibodies or both can be embedded in a specific location in the wicking pad such that the user will not need to supply that reagent. As an example, in some embodiments, the user will supply the membrane and primary antibodies, and the wicking pad will have embedded secondary antibodies or secondary reagents that will specifically bind to the primary antibodies to be used. For example, the secondary antibodies can be goat anti-rabbit antibodies linked to a detectable label for use when the primary antibody will be rabbit antibodies. It is understood that other combinations of antibodies from different species can be used. The embedded reagents will generally be embedded and dried into the wicking pad such that they are immobile until contacted by an aqueous fluid front under lateral flow and released at a user-defined events. The antibodies can be deposited in a solution that promotes their long term stability, reduced/eliminated aggregation and/or uniform release during the assay.

The wicking pad will have different regions. For example, one region, relatively closer to the second reservoir compared to other regions discussed below, will be for the placement of the membrane comprising immobilized proteins. In some embodiments, the wicking pad or the lid will have writing or drawings indicating to the user where to place the membrane. In some embodiments the wicking pad or casing could have the writing or drawings or colors or other indicators for the recommended placement of reagents, etc. The wicking pad will also have a region for applying primary antibodies (or other primary detection reagents). The region for applying primary antibodies will be closer to the first reservoir than the region for placement of the membrane. In some embodiments, the wicking pad will have writing or drawings indicating to the user where to place the primary antibodies. Optionally, as discussed above, the wicking pad can have a region for applying secondary antibodies or other secondary detection reagents for detection of the primary antibodies. The region for applying secondary antibodies or other secondary detection reagents, if present, will be located between the region for applying the primary antibodies and the first reservoir. In some embodiments, the wicking pad will have writing or drawings indicating to the user where to place the secondary antibodies or secondary detection reagents.

The second reservoir acts as a wicking "pump" for the lateral flow system and will include one or more absorbent pad encased in a water proof cover (i.e., the casing). In some embodiments, the second reservoir can be the pad. The reservoir is in liquid communication with the wicking pad (i.e., liquid, when present in the wicking pad can flow from the wicking pad to the second reservoir). The water proof cover for the second reservoir will generally not have an opening accessible to the user, but may in some embodiments have one or more hole to allow for air flow.

Figure 1:
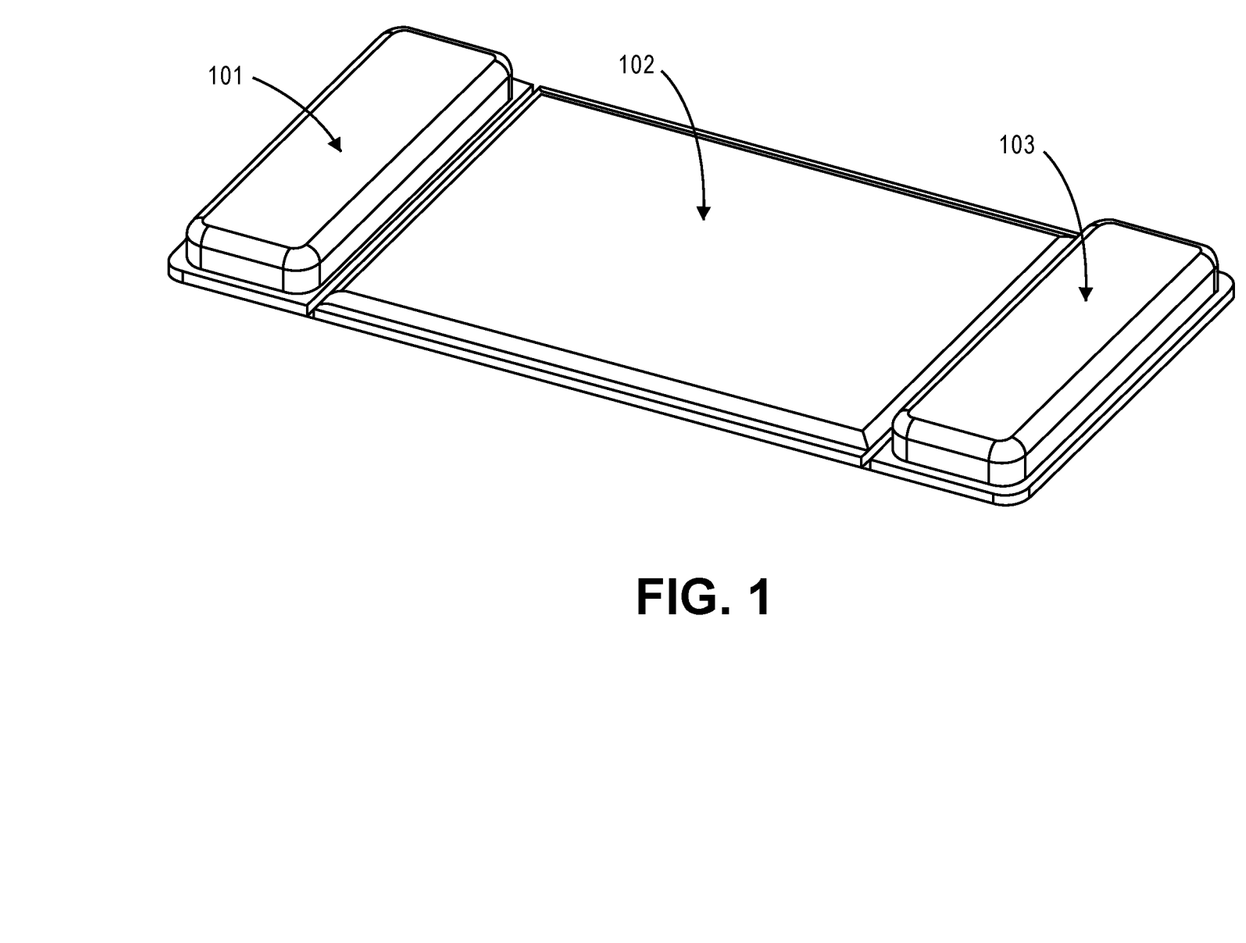
FIG. 1 depicts the outer casing for the lateral flow device described herein. The top portion of the figure shows the top of the casing. The bottom portion of the figure shows the top (left bottom) and flat bottom (bottom right) of the casing.
Figure 2:
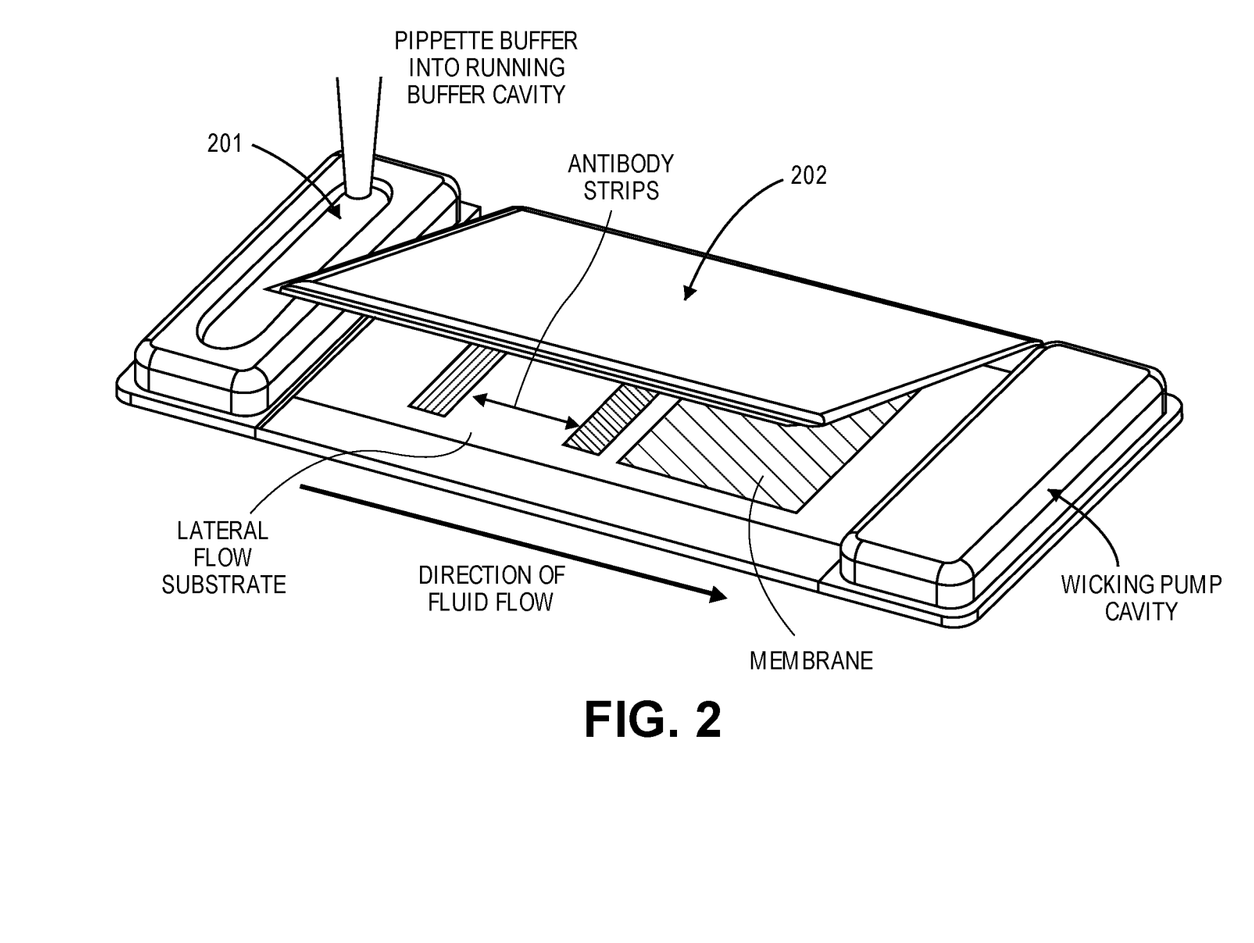
FIG. 2 depicts an embodiment of the casing and internal lateral flow apparatus. In the embodiment shown there is a port allowing for delivery of liquid into the first reservoir. A lid in the top portion of the casing over the wicking pad allows for access to the wicking pad. The lid can be opened and closed.

The above components can be contained and sealed in a waterproof casing. In some embodiments, the casing will be plastic or other inexpensive waterproof material. In some embodiments, the casing comprises a molded top portion and a flat bottom plate sealed to the top portion. The casing can for example be vacuum molded or otherwise constructed. An example of such a casing is displayed in FIG. 1. The first and second reservoirs are covered by molded portions 101 and 103. The wicking pad, being flatter, are covered by a portion of the casing depicted as 102 in FIG. 1. In some embodiments the casing does not contact the wicking pad. In some embodiments, the molded top portion comprises removable layers over the first reservoir, but not the second reservoir, to allow application of liquid. For example, FIG. 2 depicts a port 201 in the first reservoir allowing for the delivery of fluid to the first reservoir. Prior to use, the port 201 will be covered by a removable metal or plastic foil or other layer that can be readily removed by the user. The foil can be attached, for example, by an adhesive.

A portion of the top casing over the wicking pad can include a lid or other cover that can be opened and closed to provide access to the wicking pad by the user. The user can thus apply fluids to the wicking pad to moisten the wicking pad and can also apply the membrane comprising the analytes and optionally also apply detection reagents such as primary and/or secondary antibodies.

Figure 3:
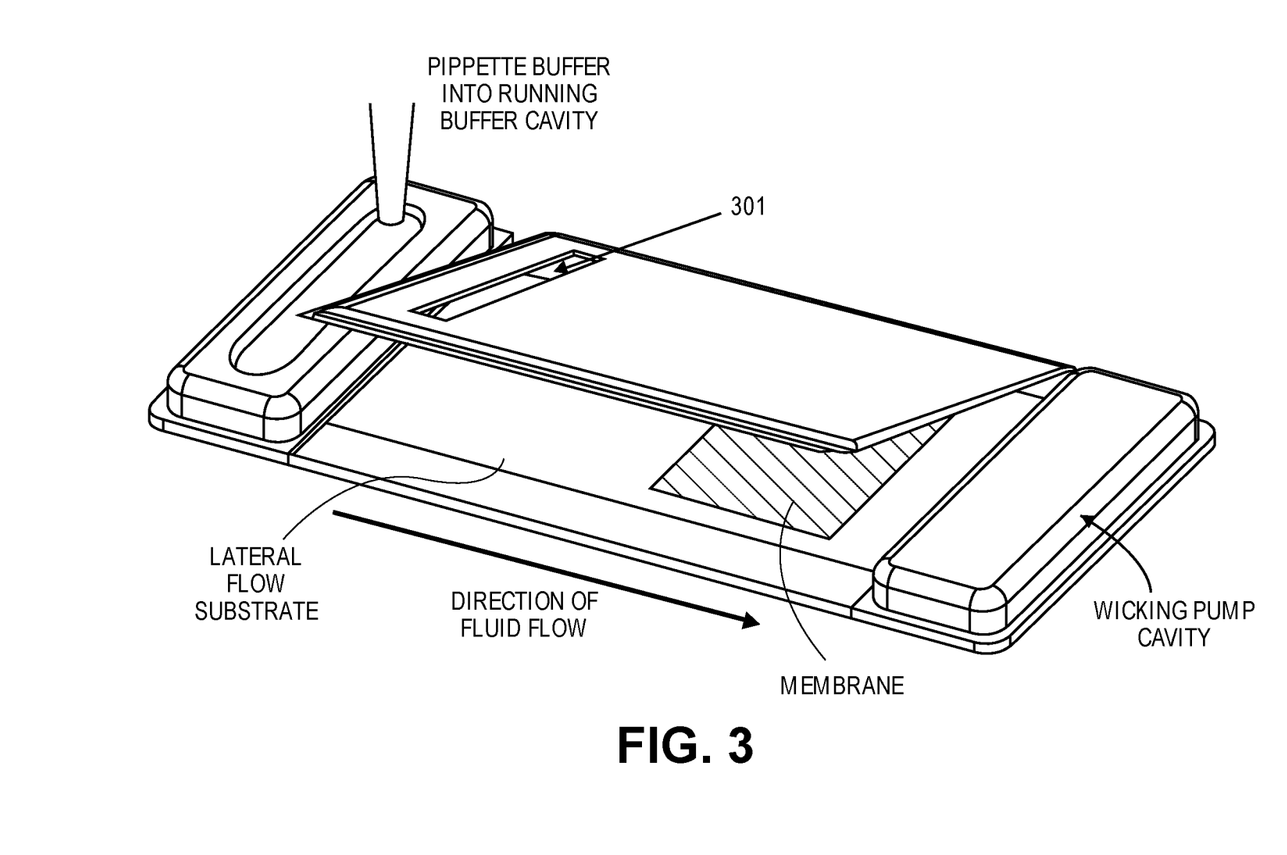
FIG. 3 depicts an embodiment of the casing and internal lateral flow apparatus. The embodiment depicted is similar to that in FIG. 2 but includes a port in the lid that allows for delivery of reagents to the wicking pad when the lid is closed. While one port is depicted, the lid could also have two or more ports.

FIG. 2 depicts a lid 202 that can be used to provide access to the wicking pad. FIG. 2 also shows an embodiment of a method of using the apparatus. In this aspect, the wicking pad is in contact with the membrane comprising analytes (e.g., western blot) and comprises primary and secondary antibodies. The wicking pad is pre-moistened by the user and running buffer is applied to the first reservoir. The running buffer is pulled by wicking from the dry second reservoir carrying the primary and then secondary antibodies into contact with the membrane. Generally, the lid will be closed once the reagents have been applied to minimize evaporation. In some embodiments, the lid over the wicking pad include one or more port for delivery of reagents to the wicking pad when the lid is closed. FIG. 3 illustrates this aspect with the port 301. FIG. 3 shows the consumable in the setup stage. In some embodiments, the user will open the center portion of the casing, wet the wicking pad with running buffer and optionally blocking buffer and fill the running buffer and optionally blocking buffer reservoir pad. The membrane will be placed face down on the wicking pad.

Figure 4:
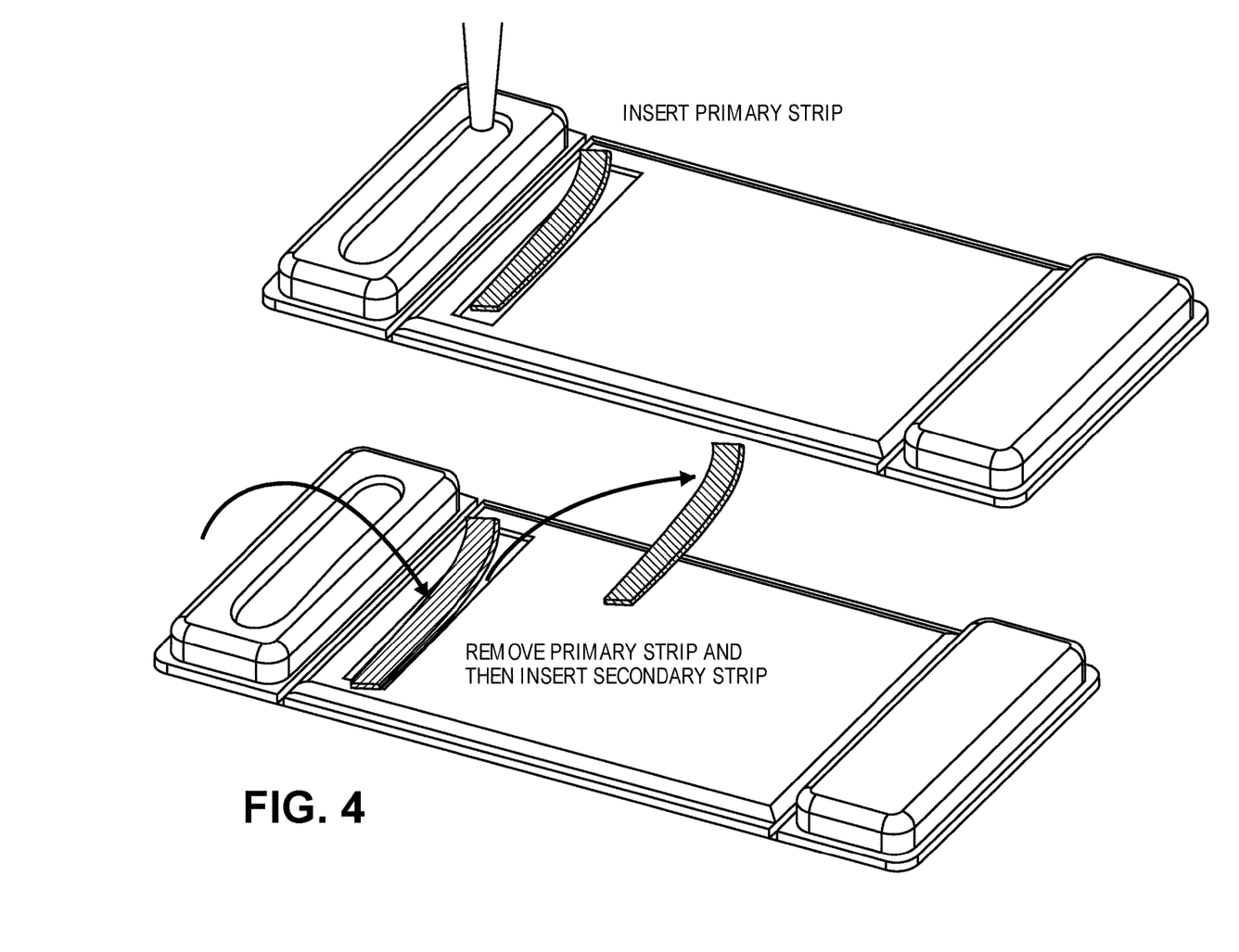
FIG. 4 depicts an embodiment of the casing and internal lateral flow apparatus. The embodiment depicted is similar to that in FIG. 3. In the top portion of FIG. 4, a strip comprising primary antibodies are applied through the port in the lid, thereby transferring primary antibodies to the (e.g., pre-moistened) wicking pad. The bottom portion of FIG. 4 shows the strip comprising primary antibodies being removed and replaced with a strip comprising secondary antibodies that are transferred to the wicking pad. Alternatively, the lid could have two ports, and the primary antibodies could be applied to one port and the secondary antibodies could be applied to a second port.

In the embodiment depicted in FIG. 4, after placement, the user will close the lid and then through the open port on the lid, will first place the primary antibody reservoir strip and allow this volume to be pulled into the lateral flow assay for sufficient time to allow the antibody to transfer to the wicking pad (e.g., 1 or more hours). The user may manually remove this strip and then place a secondary antibody reservoir strip, allowing for this volume to be pulled into the lateral flow assay for sufficient time to allow the antibody to transfer to the wicking pad (e.g., 1 or more hours). This strip can then be removed and either replaced with a final run buffer strip or left blank. This process requires a minimal user interaction with the consumable, but may experience a more sensitive result, because the two antibodies will have time to interact with the membrane with less chance of mixing during the lateral flow assay.

In some aspects, some or all detection reagents can be provided dried and/or embedded in the wicking pad. For example, in some embodiments, both primary antibodies and secondary antibodies or secondary detection reagents are embedded dry in the wicking pad. In these aspects, the user simply provides the membrane comprising the immobilized analytes and then adds running buffer to the first reservoir and optionally also the wicking pad and then allows the running buffer to move the antibodies and reagents to the membrane.

In some aspects, the user will provide some or all of the detection reagents. For example, in some embodiments, the wicking pad will include embedded secondary antibodies or secondary detection reagents and the user will provide primary antibodies. In these aspects, the user will apply the membrane comprising immobilized analytes and also primary antibodies to the wicking pad. The primary antibodies can be provided in liquid form, or alternatively, dried on a strip of a porous substrate. Exemplary porous substrates are described in, e.g., WO2015/131142. Antibodies or other reagents dried onto a strip of porous substrate can be applied at the appropriate location on the wicking pad. Once the wicking pad is moistened, the antibodies will flow from the porous substrate to the wicking pad.

In some embodiments, the porous material is glass fiber. In some embodiments, porous substrates can include, but are not limited to, polymer-containing substrates. The polymer can be in the form of polymer beads, a polymer membrane, or a polymer monolith. In some cases, the polymer is cellulose. Cellulose containing substrates include paper, cloth, woven, or non-woven cellulose substrates. Cloth substrates include those containing a natural cellulose fiber such as cotton or wool. Paper substrates include those containing natural cellulose fiber (e.g., cellulose or regenerated cellulose) and those containing cellulose fiber derivatives including, but not limited to cellulose esters (e.g., nitrocellulose, cellulose acetate, cellulose triacetate, cellulose proprionate, cellulose acetate propionate, cellulose acetate butyrate, and cellulose sulfate) and cellulose ethers (e.g., methylcellulose, ethylcellulose, ethyl methyl cellulose, hydroxyethyl cellulose, hydroxyethyl methyl cellulose, hydroxypropyl methyl cellulose, ethyl hydroxyethyl cellulose, and carboxymethyl cellulose). In some cases, the cellulose substrate contains rayon. In some cases, the substrate is paper, such as a variety of WHATMAN® paper.

Porous substrates can also include, but are not limited to, substrates that contain a sintered material. For example, the substrate can contain a sintered glass, a sintered polymer, or sintered metal, or a combination thereof. In some cases, the sintered material is formed by sintering one or more of powdered glass, powdered polymer, or powdered metal. In other cases, the sintered material is formed by sintering one or more of glass, metal, or polymer fibers. In still other cases, the sintered material is formed from the sintering of one or more of glass, polymer, or metal beads.

Porous substrates can also contain, but are not limited to, one or more non-cellulosic polymers, e.g. a synthetic polymer, a natural polymer, or a semisynthetic polymer. For example, the substrate can contain a polyester, such as polyglycolide, polylactic acid, polycaprolactone, polyethylene adipate, polyhydroxylalkanoate, polyhydroxybutyrate, poly(3-hydroxybutyrate-co-3-hydroxyvalerate, polyethylene terephthalate, polybutylene terephthalate, polytrimethylene terephthalate, polyethylene naphthalate, Vectran®. In some cases, the polymer is spunbound, such as a spunbound polyester.

Additional synthetic polymers include, but are not limited to nylon, polypropylene, polyethylene, polystyrene, divinylbenzene, polyvinyl, polyvinyl difluoride, high density polyvinyl difluoride, polyacrylamide, a ($C_2$-$C_6$) monoolefin polymer, a vinylaromatic polymer, a vinylaminoaromatic polymer, a vinylhalide polymer, a ($C_1$-$C_6$) alkyl (meth)acrylate polymer, a(meth)acrylamide polymer, a vinyl pyrrolidone polymer, a vinyl pyridine polymer, a ($C_1$-$C_6$) hydroxyalkyl (meth)acrylate polymer, a (meth)acrylic acid polymer, an acrylamidomethylpropylsulfonic acid polymer, an N-hydroxy-containing ($C_1$-$C_6$) alkyl(meth)acrylamide polymer, acrylonitrile or a mixture of any of the foregoing.

In some embodiments, the user will provide both the primary antibodies and the secondary antibodies or detection reagents (if needed). These can be provided in liquid form or in dried form in a porous strip.

The lateral flow apparatus can be provided to the user in various forms. In some embodiments, the three components (two absorbent pads (reservoirs) and a wick pad) will be shipped dry. In other embodiments one of the absorbent pads and the wick pad are supplied prewet; there would be a removable layer/barrier that connects the other absorbent pad and starts the lateral flow pump.

Other ways of introducing the antibodies or reagents to the wick pad could include reservoirs that are embedded in the lid and that contact the wick pad similar to standard lateral flow devices and familiar to those practiced in this art.

There are many absorbent bibulous pad materials, wick pad materials, and antibody application materials known in the art, the selection from which can be made to control the volume, to control the flow rate of the system, to ensure even flows, and to ensure complete delivery of antibodies/reagents from the strips. The position, width, and spacing of the strips can be optimized for the particular blotting assay as required. Other methods that affect the timing of reagent/antibody delivery such as using torturous paths in the wick pad or controlling the contact area of the antibody strips and hence the rate of antibody removal are possible. Still other embodiments to control the lateral flow process could be engineered into the plastic casing where the surface may contain sloped regions to slow or speed the flow of liquid using gravity.

In addition to zones for a primary antibody and optionally a secondary antibody or secondary detection reagents(s), it is also possible to introduce further wash zone(s) between antibodies by applying strips wet with run or other wash solution in order to facilitate still further removal of background signal and lead to sensitivity improvements in the process.

Shown in the figures is a consumable device that holds a single mini-gel sized membrane. Often users run western blots using membranes termed midi size blots which are typically 2× the width of a mini sized membrane. In other western blot applications the user may cut a mini and/or midi sized membrane into smaller sections that correspond to a few lanes of the original gel used for electrophoresis and transfer of the proteins. Therefore, the consumable lateral flow device could be of a size to accommodate either a mini or midi-sized membrane in some embodiments. In still other embodiments there could be separate ridges molded into or otherwise present in the base of the consumable where membrane sections could be placed. In this later setup up, smaller strips loaded with different antibodies may be placed at the head of each section to facilitate western blot probing of each section of membrane with a different antibody in the same device.

In other embodiments of this western blot lateral flow apparatus, antibodies may be mixed and loaded into the strips to facilitate multiplex detection of targets in a single sample.

In other embodiments, different secondary antibodies can be labeled with HRP for chemiluminescent detection, fluorescent or colorimetric tags, or other enzymes/tags depending on the desired form of detection the user prefers after the lateral flow western processing has completed.

Exemplary Detection Reagents

Binding reagents are described herein for detection of analytes. In some cases, the binding reagents are antibodies (e.g., primary or secondary antibodies). Primary antibodies can be used to bind to an analyte. In some cases, the primary antibody is labeled enabling detection of the primary antibody and consequently detection of the analyte. In some cases, the primary antibody is detected by binding to a labeled secondary binding reagent, such as a labeled secondary antibody. In some cases, tertiary binding reagents are utilized to detect complexes containing the analyte and the primary and secondary binding reagent.

ii. Labels

Analytes can be detected by detecting a label that is linked to a binding reagent. The label can be linked directly to the binding reagent (e.g., by a covalent or other bond to the primary antibody) or the attachment can be indirect (e.g., using a chelator or linker molecule). The terms "label" and "detectable label" are used synonymously herein. In some embodiments, each label (e.g., a first label linked to a first binding reagent, a second label linked to a second binding reagent, etc.) generates a detectable signal and the signals (e.g., a first signal generated by the first label, a second signal generated by the second label, etc.) are distinguishable. In some embodiments, the two or more binding reagent labels comprise the same type of agent (e.g., a first label that is a first fluorescent agent and a second label that is a second fluorescent agent). In some embodiments, the two or more binding reagent labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, colloidal gold, and combinations thereof. In some embodiments, the label can include an optical agent such as a chromophore, fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Chromophores include co-enzymes or co-factors that have a detectable absorbance. In some cases, a binding reagent can be detected by detecting the intrinsic absorbance of a peptide bond at, e.g., 220 or 280 nm.

Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. In some embodiments, 2, 3, 4, 5, or more binding reagents are each labeled with an optical agent such as a fluorescent agent (e.g., a first binding reagent labeled with a first fluorescent label, a second binding reagent labeled with a second fluorescent label, etc.), and each binding reagent that is labeled with an optical agent is detected by detecting a signal generated by the optical agent (e.g., a fluorescent signal generated by a fluorescent label). In some embodiments, all of the binding reagents are labeled with an optical agent, and each optical agent-labeled binding reagent is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{47}$Sc, $^{153}$Sr, $^{89}$Sm, $^{99m}$Tc, $^{88}$Y and $^{90}$Y. In some embodiments, 2, 3, 4, 5, or more binding reagents are each labeled with a radioisotope (e.g., a first binding reagent labeled with a first radioisotope, a second binding reagent labeled with a second radioisotope, etc.), and each binding reagent that is labeled with a radioisotope is detected by detecting radioactivity generated by the radioisotope. For example, one binding reagent can be labeled with a gamma emitter and one binding reagent can be labeled with a beta emitter. Alternatively, the binding reagents can be labeled with radionuclides that emit the same particle (e.g., alpha, beta, or gamma) at different energies, where the different energies are distinguishable. In some embodiments, all of the binding reagents are labeled with a radioisotope and each labeled binding reagent can be detected by detecting radioactivity generated by the radioisotope.

In some embodiments, the label is an enzyme, and the binding reagent is detected by detecting a product generated by the enzyme. Examples of suitable enzymes include, but are not limited to, urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some embodiments, 2, 3, 4, 5, or more binding reagents are each labeled with an enzyme (e.g., a first binding reagent labeled with a first enzyme, a second binding reagent labeled with a second enzyme, etc.), and each binding reagent that is labeled with an enzyme is detected by detecting a product generated by the enzyme. In some embodiments, all of the binding reagents are labeled with an enzyme, and each enzyme-labeled binding reagent is detected by detecting a product generated by the enzyme.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag, eXact-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length.

In some embodiments, the label is a nucleic acid barcode. As used herein a "barcode" is a short nucleotide sequence (e.g., at least about 4, 6, 8, 10, or 12, nucleotides long) that uniquely defines a labeled molecule, or a second molecule bound to the labeled binding reagent. The length of the barcode sequence determines how many unique samples can be differentiated. For example, a 4 nucleotide barcode can differentiate $4^4$ or 256 samples or less, a 6 nucleotide barcode can differentiate 4096 different samples or less, and an 8 nucleotide barcode can index 65,536 different samples or less. The use of barcode technology is well known in the art, see for example Katsuyuki Shiroguchi, et al. Digital RNA sequencing minimizes sequence-dependent bias and amplification noise with optimized single-molecule barcodes, PNAS (2012); and Smith, A M et al. Highly-multiplexed barcode sequencing: an efficient method for parallel analysis of pooled samples, Nucleic Acids Research Can 11, (2010).

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectable label (e.g., a fluorescently labeled, biotinylated, or radiolabeled alkyne or azide moiety).

Techniques for attaching detectable labels to binding reagents such as proteins (e.g., antibodies) are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

In some embodiments, two or more labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the labeled proteins). Examples of enzymes combining to generate a detectable signal include coupled assays, such as a coupled assay using hexokinase and glucose-6-phosphate dehydrogenase; and a chemiluminescent assay for NAD (P)H coupled to a glucose-6-phosphate dehydrogenase, beta-D-galactosidase, or alkaline phosphatase assay. See, e.g., Maeda et al., *J. Biolumin Chemilumin* 1989, 4:140-148.

All patents, patent applications, and other published reference materials cited in this specification are hereby incorporated herein by reference in their entirety. As used in this specification and the appended claims, the singular forms "a", "an", and "the" include plural referents unless the content clearly dictates otherwise.

What is claimed is:

1. A lateral flow apparatus comprising,
    a wicking pad composed of a porous substrate, the wicking pad having:
    (i) markings indicating a region for applying a membrane comprising immobilized analytes; and
    (ii) a region for applying primary antibodies; and
    wherein the wicking pad has a first edge and a second edge and two lateral edges,
    a first reservoir comprising a first absorbent pad adjacent to the first edge of the wicking pad; and
    a second reservoir comprising a second absorbent pad adjacent to the second edge of the wicking pad;
    wherein the apparatus is sealed in a plastic casing, the plastic casing comprising a molded top portion and a flat bottom plate sealed to the top portion; and
    wherein the molded top portion comprises a port covered by a removable layer over the first reservoir to allow application of liquid and optionally the molded top portion comprises a port covered by a removable layer over the second reservoir to allow for air flow.

2. The apparatus of claim 1, wherein the analytes are proteins.

3. The apparatus of claim 1, wherein the wicking pad further comprises:
    (iii) a region for applying secondary antibodies or other secondary detection reagents.

4. The apparatus of claim 1, wherein the removable layer is composed of a metal or plastic foil.

5. The apparatus of claim 1, wherein the molded top portion comprises a lid over the regions (i), (ii), and (iii) to allow for access to the regions and subsequent closing of the lid.

6. The apparatus of claim 5, wherein the lid comprises a port to allow for delivery of reagents through the port to the wicking pad when the lid is closed.

7. The apparatus of claim 1, wherein the region for applying primary antibodies is between the first reservoir and the region for applying a membrane comprising proteins, and wherein the molded top portion of the plastic casing:
    has a user-accessible port to allow for delivery of liquid to the first reservoir and
    (i) lacks a user-accessible port to access the second reservoir and optionally has holes in the casing surrounding the second reservoir to allow for air flow, or
    (ii) has a user-accessible port around the second reservoir to allow for air flow.

8. The apparatus of claim 1, wherein at least one of the reservoirs is separated from the wicking pad by a removable non-absorbent strip.

9. The apparatus of claim 1, wherein the wicking pad and reservoirs are dry.

10. The apparatus of claim 1, wherein at least one of the wicking pad, the first reservoir, and the second reservoir is wet.

11. The apparatus of claim 3, wherein the region for applying secondary antibodies on the wicking pad comprises dried secondary antibodies embedded in the wicking pad.

12. The apparatus of claim 1, wherein the region for applying primary antibodies on the wicking pad comprises dried primary antibodies embedded in the wicking pad.

13. A kit for lateral flow, the kit comprising, the apparatus of claim 1.

14. A method of performing a lateral flow western blot assay, the method comprising;
    providing a lateral flow apparatus comprising,
        a wicking pad composed of a porous substrate, the wicking pad having:
        (i) markings indicating a region for applying a membrane comprising immobilized analytes; and
        (ii) a region for applying primary antibodies; and
        wherein the wicking pad has a first edge and a second edge and two lateral edges,
        a first reservoir comprising a first absorbent pad adjacent to the first edge of the wicking pad; and
        a second reservoir comprising a second absorbent pad adjacent to the second edge of the wicking pad;
    applying running buffer to the first reservoir and the wicking pad;
    applying a membrane comprising proteins to the region (i) for applying a membrane comprising proteins;
    applying primary antibodies to the region (ii) for applying primary antibodies; and
    allowing lateral flow of the running buffer from the first reservoir to the second reservoir such that the primary antibodies are transported in the wicking pad and are contacted to the proteins in the membrane, wherein the primary antibodies bind to their target proteins, if present, in the membrane.

15. The method of claim 14, wherein the apparatus is sealed in a plastic casing, wherein the plastic casing comprises a molded top portion and a flat bottom plate sealed to the top portion and the molded top portion comprises removable a layer over the first reservoir to allow application of liquid and a lid over the regions (i) and (ii) to allow for access to the regions and subsequent closing of the lid; and
    the method further comprises:
    removing the layer over the first reservoir and applying running buffer to the first reservoir; and
    opening the lid and applying running buffer and the membrane to the wicking pad and subsequently closing the lid to allow for lateral flow from the first reservoir to the second reservoir.

16. The method of claim 14, wherein said applying primary antibodies to the region (ii) for applying primary antibodies comprises contacting a porous strip comprising dried embedded primary antibodies to the wicking pad such that the primary antibodies are eluted from the porous strip to the wicking pad.

17. The method of claim 14, further comprising applying secondary antibodies or secondary detection reagents to the wicking pad such that the secondary antibodies or secondary detection reagents flow by lateral flow through the wicking pad and into the membrane after the primary antibodies contact the membrane.

* * * * *